United States Patent [19]

Yoshioka et al.

[11] Patent Number: 4,563,425

[45] Date of Patent: Jan. 7, 1986

[54] ENZYME REACTION METHOD FOR ISOMERIZATION OF GLUCOSE TO FRUCTOSE

[75] Inventors: Toshio Yoshioka; Kazuo Teramoto; Masaharu Shimamura, all of Otsu, Japan

[73] Assignee: Toray Industries, Inc., Tokyo, Japan

[21] Appl. No.: 596,101

[22] Filed: Apr. 2, 1984

Related U.S. Application Data

[62] Division of Ser. No. 355,240, Mar. 5, 1982, abandoned.

[30] Foreign Application Priority Data

Mar. 19, 1981 [JP] Japan ................................ 56-39930

[51] Int. Cl.[4] ...................... C12P 19/24; C12N 11/02; C12N 11/08; C12N 9/96
[52] U.S. Cl. ..................................... 435/94; 435/176; 435/177; 435/179; 435/180; 435/182; 435/188
[58] Field of Search ................ 435/94, 174, 176, 177, 435/178, 179, 180, 181, 182, 188

[56] References Cited

U.S. PATENT DOCUMENTS

| | | | |
|---|---|---|---|
| 3,960,663 | 6/1976 | Tamura et al. | 435/94 |
| 3,982,997 | 9/1976 | Eaton et al. | 435/94 |
| 4,008,124 | 2/1977 | Fujita et al. | 435/94 |
| 4,025,389 | 5/1977 | Borge et al. | 435/94 |
| 4,208,482 | 6/1980 | Ehventhal et al. | 435/94 X |
| 4,246,350 | 1/1981 | Hier et al. | 435/180 |
| 4,263,400 | 4/1981 | Ushiro | 435/94 X |
| 4,264,732 | 4/1981 | Lartigan et al. | 435/94 |

*Primary Examiner*—David M. Naff
*Attorney, Agent, or Firm*—Austin R. Miller

[57] ABSTRACT

A metal ion that inhibits enzyme deactivation is bonded to a carrier and inhibits enzyme deactivation when contacted with a substrate for the enzyme. A carrier-bound metal ion such as ions of iron is particularly suitable for inhibiting deactivation of glucose isomerase when isomerizing glucose to fructose. Glucose isomerase life is remarkably prolonged by contacting carrier-bound iron ions with a glucose substrate solution prior to isomerizing with glucose isomerase.

21 Claims, No Drawings

4,563,425

ENZYME REACTION METHOD FOR ISOMERIZATION OF GLUCOSE TO FRUCTOSE

BACKGROUND OF THE INVENTION

This is a division of application Ser. No. 355,240, filed 3/5/82, now abandoned.

This invention relates to an enzyme deactivation inhibitor and an enzyme reaction method. Enzymes are widely utilized as a specific catalyst for a variety of industrial treatments and processes. Among such enzymes, glucose isomerase is of especially high utility, being capable of reversible interconversion of glucose and fructose. Glucose isomerase is generally utilized for the industrial production of fructose-containing syrup by isomerizing glucose. Enzymes such as glucose isomerase have been generally used by immobilizing the enzyme itself or the enzyme-containing fungus body according to a known insolubilization method such as a conjunction method or an inclusion method so that the enzyme can be used repeatedly. Therefore, it is a matter of great importance for the enhancement of productivity to prevent deactivation of the enzyme in the isomerization reaction step, thereby prolonging its effective life. As a means for preventing deactivation of glucose isomerase, there has been proposed a method according to which a soluble iron salt and a magnesium salt are dissolved in the substrate solution for the isomerization reaction to let the iron ions coexist with the magnesium ions (U.S. Pat. No. 4,008,124 issued Feb. 15, 1977). According to this method, however, coloration or sedimentation of the substrate results due to addition of iron ions and removal of the iron ions after termination of the reaction is troublesome. Further, no satisfactory effect is provided where industrial refined glucose is used as the substrate.

BRIEF DESCRIPTION OF THE INVENTION

The present inventors have pursued further researches on effective means for preventing deactivation of glucose isomerase, particularly where industrial refined glucose is used as the substrate and, as a result, have reached the present invention.

Thus, the present invention provides:

(1) an enzyme deactivation inhibitor in which the ions of a metal or metals capable of assuming at least two different states of oxidation are bonded to a carrier, and (2) a method for effecting an enzyme reaction by contacting a glucose-containing substrate solution with an enzyme, characterized in that said substrate solution is contacted, before termination of said reaction, with a carrier to which the ions of a metal or metals capable of assuming at least two different states of oxidation have been bonded.

It has been found that when an isomerization reaction is carried out after contacting an aqueous glucose solution with the enzyme deactivation inhibitor of this invention, quite surprisingly, the enzyme life is remarkably prolonged.

The object of this invention is to provide an enzyme deactivation inhibitor, that is, a compound effective for preventing deactivation of enzyme, and a method for performing an enzyme reaction for a prolonged period of time by contacting the glucose-containing substrate solution with the inhibitor before termination of the enzyme reaction.

DETAILED DESCRIPTION OF THE INVENTION

Regarding first the carriers used in this invention for bonding with the ions of a metal or metals capable of assuming at least two different states of oxidation, there may be employed known types of carriers capable of bonding to the metal ions, such as for example polysaccharides and derivatives thereof, polyamides, glass, ion exchangers, etc. Ion exchangers are particularly preferred as they can form ionic bonds or coordinate bonds with said metal ions at a high bonding rate. As such ion exchangers, there may be employed known inorganic ion exchangers such as permutite, zeolite, aluminosilicate, etc., natural ion exchangers such as polysaccharide, and known organic ion exchangers prepared by introducing an ion exchange group onto a synthetic organic polymer such as styrene, phenol, vinyl alcohol, acrylic and other like types of polymers. Among them, the synthetic organic ion exchangers are preferred because of a high rate of bonding with the metal ions, low susceptibility to attack of microorganisms and high physical strength. Particularly preferred are styrene-based synthetic organic ion exchangers because of their high chemical and heat resistance.

As the ion exchange group, there may be used an anion exchange group such as an amino group, a cation exchange group such carboxylic acid, phosphoric acid, sulfonic acid groups etc., and other known chelate groups capable of forming coordinate bonds with the metal ions such as hydroxyl, carboxyl, polycarboxylic acid, aldehyde, polyamino, amino carboxylic acid, peptide, $\beta$-diketone groups, etc., and these ion exchange groups may be used in combination. Among them, the amino, carboxylic acid, phosphoric acid, sulfonic acid, polyamino and amino carboxylic acid groups are preferred as they are easily bonded to the metal ions and can also give a high deactivation inhibitory effect. Particularly preferred are polyamino groups such as $-NH(C_2H_4NH)_nH$ (where n is a number of 1 or greater) and $-NH(CH_2)_mNH_2$ (where m is a number of 3 to 12) and amino carboxylic acid groups such as the iminodiacetic acid group and polyaminopolyacetic acid group because of their high stability of bonding to the metal ions and high deactivation preventive effect. Introduction of the ion exchange group may be accomplished by any known suitable method. The carrier to which the metal ions are bonded is usually of an insoluble type, but it is possible to use a soluble type carrier where it is gelled after being bonded to the metal salt.

As the metals capable of assuming at least two different states of oxidation in this invention, there may be cited titanium, vanadium, chromium, manganese, iron, cobalt, copper, tin, cerium and silver. These metals may be used in an admixture of two or more. Among them, iron, cobalt and copper are preferred because of their high enzyme deactivation preventive effect and low cost. Iron is especially favored as it can give an extremely high effect and presents no food sanitation problems.

The enzyme deactivation inhibitor according to this invention is produced by reacting the metal salt with the carrier so that the metal ions are bonded to the carrier. The metal salt used in this invention may be selected from acid salts and complex salts such as halogen salts, sulfates, acetates, etc. Easily soluble acid salts are preferably used. The reaction between the metal salt and the carrier can be accomplished by contacting the carrier and metal salt in solution. Where an insoluble carrier is used, the desired reaction may be accomplished by passing a metal salt solution through a column packed with the carrier. The reaction is usually conducted by using 0.01 to 2 M/l of a metal salt solution at room temperature for a period of from 1 minute to 40 hours. After completion of the reaction, the reaction mixture is washed with water or various types of buffer solution, such as citrate buffer solution, Veronal buffer solution, acetate buffer solution, phosphate buffer solution, tris buffer solution, glycine buffer solution, Menzel buffer solution, etc. to remove any unreacted salts.

In the enzyme deactivation inhibitor of this invention, the metal is contained in an amount of at least 0.01 meq/g, preferably more than 0.1 meq/g, and particularly preferably within the range of from 0.5 to 2.5 meq/g. A lesser content of metal results in an unsatisfactory effect of the inhibitor. Although no specific restriction is imposed on the upper limit for the metal content, it is difficult and impractical to effect bonding at a rate exceeding 2.5 meq/g.

The enzyme deactivation inhibitor of this invention is usually used in the form of powder, fine grains, resinous grains, fibers, hollow fibers, films, paper, etc. Among such forms, the resinous grain and fiber forms are preferred as they are easy to treat. Especially, macroreticular or porous resinous grain and fiber forms are preferred because of the large active surface area. Where fibers are used, core-sheath type composite fibers using various known types of fiber forming polymers such as polyamide, polyester, poly-α-olefin, polyacrylonitrile or copolymers thereof as core component, the multiple core type composite fiber and the simple mixed fiber are favored because of high mechanical strength, and among them the multiple core type composite fiber and simple mixed fiber are most preferred because of their excellent durability. The product may be also used in known suitable forms such as knitted fabric, braid, felt, etc.

The enzyme deactivation inhibitor according to this invention proves particularly effective for preventing deactivation of the enzyme in an enzyme reaction using a substrate solution containing a reducing sugar such as glucose. It is also possible to use two or more types of the enzyme deactivation inhibitor of this invention in admixture or in combination. When the deactivation inhibitor of this invention has lost most of its efficacy after long-time use, it may be regenerated by treating it with a water-soluble salt, a mineral acid, an alkaline solution or a mixed solution or a combination thereof according to the type of the carrier used and again reacting it with the metal salt to produce the enzyme deactivation inhibitor of this invention.

For the enzyme reaction method according to this invention, by mixing at least one enzyme deactivation inhibitor having its carrier bonded to the ions of a metal or metals capable of assuming at least two different states of oxidation with an enzyme or an insolubilized enzyme, or by using an insolubilized enzyme prepared by bonding, mixing or compounding the inhibitor with an enzyme such that the content of the metal is within the range of 0.05 to 2 meq/g, preferably 0.1 to 1 meq/g, the substrate solution containing glucose is contacted with the enzyme deactivation inhibitor while simultaneously performing the enzyme reaction. Alternatively, the glucose-containing substrate solution is contacted with at least one said enzyme deactivation inhibitor prior to the enzyme reaction and then the enzyme reaction is carried out. The latter method is preferred as it provides a higher enzyme deactivation inhibitory effect and this permits the enzyme reaction to continue over an extended period of time. The methods may be used in combination. In the latter method, the glucose-containing substrate solution may be contacted with the enzyme deactivation inhibitor at any stage preceding the enzyme reaction, but it is most effective and hence most desirable to effect the contact just before commencing the enzyme reaction.

Various methods may be employed for contacting the glucose-containing substrate solution with the enzyme deactivation inhibitor, such as a batch method in which the inhibitor is added to the substrate solution and stirred, a fixed bed method in which the substrate solution is passed through the layers filled with the inhibitor to such a density as to allow easy passage of the solution according to the form used, and a continuous method. The fixed bed method is particularly preferred as it allows contact of a large volume of substrate solution with case.

The glucose concentration in the substrate solution is usually about 1 to 70% by weight. If it is too low, the throughput rate increases, while if it is too high, passage of the solution is retarded. Thus, the glucose concentration should preferably be within the range of about 5 to 60% by weight. The contact temperature is usually about 10° to 100° C. Too low a contact temperature causes an increased viscosity of the solution which decreases its fluidity and necessitates a longer time of contact, while too high a contact temperature may cause decomposition or denaturing of the glucose and/or substrate. The preferred range of contact temperature is from about 20° to 80° C.

The time of contact between the enzyme deactivation inhibitor and the glucose-containing substrate solution should be suitably determined according to the type of the inhibitor used, metal content, substrate solution concentration, contact temperature and other factors so as to provide the maximum enzyme deactivation inhibitory effect, but usually the contact time is within the range of about 0.1 to 1,000 ml/g hr, preferably 1 to 500 ml/g hr. If the contact time is outside this range, satisfactory enzyme deactivation inhibitory effect may not be provided and denaturing of glucose or substrate may be caused. The enzyme reaction is preferably carried out at a known substrate concentration, temperature and pH pertinent to the enzyme or insolubilized enzyme to be treated.

The enzyme reaction using a glucose-containing substrate solution according to this invention, may be accomplished in various ways, which include the following methods: the glucose solution is isomerized with immobilized glucose isomerase to produce a fructose-containing syrup; a liquefied starch or a starch solution which has undergone partial saccharification after liquefaction is further saccharized with immobilized glycoamylase to produce glucose; a cellulose solution formed by partially saccharizing and dissolving cellulose is further saccharized with immobilized cellulase to produce glucose; and a glucose solution is treated with zymase-containing yeast or immobilized yeast to produce an alcohol. The effect of this invention, however, is maximized when using the reaction pattern in which a glucose solution is isomerased with immobilized glucose isomerase to produce a fructose-containing syrup. More specifically, 30 to 60% by weight of a glucose solution (pH 6.5–9.0) containing 0.1–20 mM/l of magnesium ions is passed through a single bed or several fixed beds composed of first-stage layers packed with the enzyme deactivation inhibitor at the required density according to the type thereof and is then passed through second-stage layers of immobilized glucose isomerase at a temperature of 55°–70° C. and with a contact time selected to provide the desired isomerization rate. This glucose isomerization reaction method is particularly preferred for producing the maximum effect of the invention, but the present invention is not restricted to such a reaction method.

As for the immobilized glucose isomerase used in this invention, there may be employed various known types; for example, a preparation formed by immobilizing an enzyme-containing fungus body or an extracted enzyme on an insolubilized material such as quaternary vinyl-pyridine resin, DEAE-cellulose, porous alumina, polyphenolic anion exchange resin, styrenedivinylbenzene-based macro-reticular or porous anion exchange resin, anion exchange fiber, and a fiber having a specific group (Japanese Patent Laid-Open No. 6774/75, U.S. Pat. No. 3,788,945 Japanese Patent Laid-Open Nos. 110889/74, 80160/74, 53582/75, 15019/79 and 98912/80), a preparation formed by crosslinking an enzyme-containing fungus body with glutaraldehyde (Japanese Patent Laid-Open No. 9227/74), and a preparation obtained by incorporating an extracted enzyme in cellulose acetate and spinning the mixture into fiber (Japanese Patent Laid-Open No. 82084/73). Among them, the preparation formed by immobilizing an extracted enzyme on a fiber is particularly preferred because of the high enzyme activity.

The present invention is further described by way of the following examples, but these examples are merely intended to be illustrative and not restrictive to the scope of the invention.

EXAMPLE 1

By using polypropylene (Mitsui Noblen J-3-HG) as an island component and a mixture of 51.7 parts of polystyrene (Styron 679), 1.5 parts of low-molecular polystyrene (Hymer ST-120), 5.3 parts of polypropylene (Mitsui Noblen WF-727-D) and 0.6 parts of low-molecular weight polypropylene (Viskole 550-P) as a sea component, the sea and island components were mixed at a sea:island ratio of 59.1:40.9 and subjected to melt composite spinning (the number of islands: 18) at 255° C. and the resulting filaments were stretched 5 times the original length to obtain multi-core sea-and-island type composite fiber (single filament size: 1.9 d, tenacity: 2.5 g/d). 1.0 part of the fiber in the form of a braid was added to a solution composed of 1.0 part of methylolacrylamide, 10 parts of sulfuric acid, 10 parts of nitrobenzene and 0.03 parts of paraformaldehyde and reacted at room temperature for 4 hours. The reaction product was extracted with methanol and an acrylamidomethyl group was introduced to the polystyrene portion simultaneously with crosslinking. Then the product was further treated in 20% diethylenetriamine-methanol under reflux for 6 hours to introduce a polyamino group. After conversion into a free type, the product was added to 100 parts of a 50 mM/l ferric chloride solution and reacted with stirring at room temperature for 4 hours. The reaction product was washed with water and further treated with a phosphate buffer solution of pH 7 and then with a sodium hydrogen carbonate buffer solution of pH 8.2 to obtain 2.2 parts of an enzyme deactivation inhibitor according to this invention. The iron content was 0.89 meq/g.

An immobilized preparation of glucose isomerase (available from Novo Inc. of Denmark under the trade name "Sweetzyme-Q") was packed in a column having 1.6 cm inner diameter, immersed in a thermostatic tank and the enzyme deactivation inhibitor was further packed in the upper layer portion thereof. A substrate solution (pH 8.2) composed of an industrial refined dextrose solution containing 5 mM/l of magnesium sulfate and 3M/l of glucose was passed through the column from the top continuously for 30 days at a temperature of 61° C. and at a flow rate of approximately 20 ml/hr, and the half-life of the enzyme was determined. The results are shown in Table 1. The half-life of the enzyme was determined according to the method shown in Japanese Patent Publication No. 12238/80, that is, the activity index was determined every other day or on every third day, and since the activity index lowers as an exponential function of the number of days of passing of the solution due to deactivation of the enzyme, the half-life was calculated in terms of the days in which the activity index became half (50%) of the original figure by using the method of least squares.

EXAMPLE 2

An acrylamidomethyl group was introduced to 1.0 part of the above-described braid-like molded multi-core sea-and-island type composite fiber according to the method of Example 1. Then the reaction product was further treated in 20% pentaethylenehexamine-methanol under reflux for 6 hours to introduce a polyamino group. After conversion into a free type, the product was added to 100 parts of a 50 mM/l aqueous solution of ferric chloride and reacted with stirring at room temperature for 4 hours. The reaction product was washed with water and then treated with a trissulphate buffer solution of pH 8.0 to obtain 2.4 parts of an enzyme deactivation inhibitor of this invention. The iron content was 0.86 meq/g. By using the thus-obtained inhibitor, a substrate solution was passed through a column in the same manner as described in Example 1, except for continuous 7-day passing of the solution at 66° C., to obtain a fructose-containing syrup. The half-life of the enzyme was determined according to the method of Example 1. The results are shown in Table 1.

EXAMPLE 3

After introducing a polyamino group to 1.0 part of the braid-like molded multi-core sea-and-island type composite fiber according to the method of Example 1, the reaction product was further treated with a solution consisting of 6 parts of monochloroacetic acid, 3.5 parts of potassium hydroxide, 6 parts of potassium carbonate, 30 parts of methanol and 10 parts of water under reflux for 6 hours to introduce a polyaminopolyacetic acid group. After additional treatment with an acetate buffer of pH 5, the product was reacted with an iron salt and treated with buffer solutions in the same manner as described in Example 1 to obtain 2.4 parts of an enzyme deactivation inhibitor of this invention. The iron content was 0.94 meq/g. The half-life of the enzyme was determined according to the same method as in Example 2 except for use of the inhibitor of this example instead of the inhibitor obtained in Example 2. The results are shown in Table 1.

EXAMPLE 4

10 ml of a commercial chelate resin having an iminodiacetic acid group (trade name: Diaion CR-10) was buffered with sodium hydrogencarbonate of pH 8.2 and the product was reacted with an iron salt for 20 hours and further treated with buffer solutions in the manner described in Example 1 to obtain 2.4 parts of an enzyme deactivation inhibitor of this invention. The iron content was 1.43 meq/g. By using the thus-obtained inhibitor, the half-life of the enzyme was determined according to the method of Example 2. The results are shown in Table 1.

EXAMPLE 5

A polyamino group was introduced to 1.0 part of the braid-like molded multi-core sea-and-island type composite fiber according to the method of Example 2. After treatment with an acetate buffer solution of pH 5.0, the product was added to 100 parts of an acetate buffer solution of pH 5.0 containing 50 mM/l of cobalt acetate, reacted with stirring at room temperature for 4 hours and, after washing with water, treated with a tris-sulfate buffer solution of pH 8.0 to obtain 2.3 parts of an enzyme deactivation inhibitor of this invention. The cobalt content was 0.76 meq/g. By using the thus-obtained inhibitor, the half-life of the enzyme was determined in the same way as in Example 1 except that a column of 1.0 cm inner diameter was used and continuous 7-day passing of the solution was carried out at a flow rate of approximately 10 ml/hr and at a temperature of 67° C. to produce a fructose-containing syrup. The results are shown in Table 1.

EXAMPLE 6

2.4 parts of an enzyme deactivation inhibitor of this invention was obtained according to the method of Example 5, using copper sulfate instead of cobalt acetate. The copper content was 1.28 meq/g. The half-life of the enzyme was determined in the same manner as in Example 5 except that the inhibitor of this example was used instead of the inhibitor of Example 5. The results are shown in Table 1.

COMPARATIVE EXAMPLE 1

The half-life of the enzyme without use of the enzyme deactivation inhibitor of this invention was determined as in Example 1. The results are shown in Table 1.

COMPARATIVE EXAMPLE 2

The half-life of the enzyme without use of the enzyme deactivation inhibitor of this invention but with 0.1 mM/l of iron sulfate added to the substrate solution was determined as in Example 2. The results are shown in Table 1. The addition of iron sulfate caused coloration of the substrate solution and a sediment was formed in the column as the reaction continued over a period of days, decreasing flow of the solution.

COMPARATIVE EXAMPLE 3

The half-life of the enzyme without use of the enzyme deactivation inhibitor of this invention was determined as in Example 2. The results are shown in Table 1.

COMPARATIVE EXAMPLE 4

The half-life of the enzyme without use of the enzyme deactivation inhibitor of this invention was determined as in Example 5. The results are shown in Table 1.

It is apparent from Table 1 that the life of insolubilized enzyme is remarkably prolonged by performing an enzyme reaction after contacting the substrate solution with a small quantity of an enzyme deactivation inhibitor according to this invention.

TABLE 1

| | Enzyme deactivation inhibitor of this invention | | | | Amount of immobilized enzyme preparation used (g) | Reaction temperature (°C.) | Half-life of enzyme (days) |
| --- | --- | --- | --- | --- | --- | --- | --- |
| | Metal ion | Group bonded to metal ions | Form | Amount used (g) | | | |
| Example 1 | Iron | —NH(C$_2$H$_4$NH)$_2$H | Fiber | 1.0 | | | 56 |
| Comparative Example 1 | No inhibitor used | | | | 4.0 | 61 | 32 |
| Comparative Example 2 | No inhibitor used, but 0.1 mM/l of iron sulfate was added to the substrate solution | | | | | | 40 |
| Example 2 | | —NH(C$_2$H$_4$NH)$_5$H | Fiber | 0.28 | 2.8 | 66 | 31 |
| Example 3 | Iron | Polyaminopolyacetic acid group | | | | | 25 |
| Example 4 | | Iminodiacetic acid group | Resin | 0.38 | | | 31 |
| Comparative Example 3 | No inhibitor used | | | | | | 16 |
| Example 5 | Cobalt | —NH(C$_2$H$_4$NH)$_5$H | Fiber | 0.14 | | | 23 |
| Example 6 | Copper | | | | 1.4 | 67 | 18 |
| Comparative Example 4 | No inhibitor used | | | | | | 13 |

We claim:

1. In an enzyme isomerization reaction method in which a glucose-containing substrate solution is contacted with an immobilized glucose isomerase to produce a fructose-containing syrup, the improvement comprising, prior to the isomerization reaction, contacting said substrate solution with a synthetic organic ion exchanger to which ions of iron are bonded.

2. An enzyme reaction method according to claim 1, wherein said substrate solution is passed through layers filled with said ion exchanger.

3. An enzyme reaction method according to claim 1, wherein said immobilized glucose isomerase is formed by immobilizing an isomerase-containing fungus body on an insolubilized material.

4. An enzyme reaction method according to claim 3, wherein said insolubilized material is selected from the group consisting of quaternary vinyl pyridine resin, DEAE-cellulose, porous alumina, polyphenolic anion exchange resin, styrene-divinylbenzene-based macro-reticular or porous anion exchange resin, anion exchange fiber and mixtures thereof.

5. An enzyme reaction method according to claim 1, wherein a solution containing 30 to 60% by weight of glucose and 0.1~20 mM/l of magnesium ions is passed through at least one fixed bed composed of first-stage layers packed with said synthetic organic ion exchanger containing said bound iron ions and then through second-stage layers of said immobilized glucose isomerase at a temperature of 55°–70° C.

6. An enzyme reaction method according to claim 1, wherein said synthetic organic ion exchanger is styrene-based.

7. An enzyme reaction method according to claim 6, wherein said ion exchanger has at least one ion exchange group selected from the group consisting of amine, carboxylic acid, phosphoric acid, sulfonic acid, hydroxyl, carboxyl, polycarboxylic acid, aldehyde, polyamino, amino carboxylic acid, peptide, $\beta$-diketone groups and mixtures thereof.

8. An enzyme reaction method according to claim 7, wherein said ion exchange group is selected from the group consisting of amino, carboxylic acid, phosphoric acid, sulfonic acid, polyamino, amino carboxylic acid groups and mixtures thereof.

9. An enzyme reaction method according to claim 8, wherein said polyamino group is selected from the group consisting of —NH($C_2H_4$NH)$_n$H (where n is a number of 1 or greater), —NH($CH_2$)$_m$NH$_2$ (where m is a number of 3 to 12) and mixtures thereof.

10. An enzyme reaction method according to claim 8, wherein said amino carboxylic acid group is selected from the group consisting of iminodiacetic acid group, polyaminopolyacetic acid group and mixtures thereof.

11. An enzyme reaction method according to claim 1, wherein the amount of said iron ions is at least 0.01 meq/g of said ion exchanger.

12. An enzyme reaction method according to claim 11, wherein the amount of said iron ions is greater than 0.1 meq/g of said ion exchanger.

13. An enzyme reaction method according to claim 11, wherein the amount of said iron ions is within the range of from 0.5 to 2.5 meq/g of said ion exchanger.

14. An enzyme reaction method according to claim 1, wherein said ion exchanger is in a form selected from the group consisting of powder, fine grains, resinous grains, fibers, hollow fibers, film, paper and mixtures thereof.

15. An enzyme reaction method according to claim 14, wherein said resinous grains are selected from macro-reticular and porous resinous grains.

16. An enzyme reaction method according to claim 14, wherein said fibers are composed of a fiber forming polymer.

17. An enzyme reaction method according to claim 16, wherein said fiber forming polymer is at least one polymer selected from the group consisting of polyamide, polyester, poly-$\alpha$-olefine, polyacrylonitrile and copolymers thereof.

18. An enzyme reaction method according to claim 1, wherein said immobilized glucose isomerase is formed by immobilizing an extracted isomerase on an insolubilized material.

19. An enzyme reaction method according to claim 1, wherein said immobilized glucose isomerase is formed by crosslinking an isomerase-containing fungus body with glutaraldehyde.

20. An enzyme reaction method according to claim 1, wherein said immobilized glucose isomerase is formed by incorporating extracted isomerase in cellulose acetate and spinning the mixture into a fiber.

21. An enzyme reaction method according to claim 1, wherein said immobilized glucose isomerase is formed by a method selected from the group consisting of immobilizing an extracted isomerase on an insolubilized material, crosslinking an isomerase-containing fungus body with glutaraldehyde, and incorporating extracted isomerase in cellulose acetate and spinning the mixture into a fiber.

* * * * *

UNITED STATES PATENT AND TRADEMARK OFFICE
CERTIFICATE OF CORRECTION

PATENT NO. : 4,563,425

DATED : Jan. 7, 1986

INVENTOR(S) : T. Yoshioka; K. Teramoto and M. Shimamura

It is certified that error appears in the above-identified patent and that said Letters Patent is hereby corrected as shown below:

Column 9, line 22, delete "amine" and insert --amino--.

Signed and Sealed this

Fourteenth Day of April, 1987

Attest:

DONALD J. QUIGG

Attesting Officer

Commissioner of Patents and Trademarks